(12) United States Patent
Mukumoto

(10) Patent No.: US 9,538,972 B2
(45) Date of Patent: Jan. 10, 2017

(54) X-RAY CT APPARATUS

(71) Applicant: Toshiba Medical Systems Corporation, Otawara-shi (JP)

(72) Inventor: Go Mukumoto, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 298 days.

(21) Appl. No.: 14/110,860

(22) PCT Filed: Jan. 21, 2013

(86) PCT No.: PCT/JP2013/051108
§ 371 (c)(1),
(2) Date: Oct. 9, 2013

(87) PCT Pub. No.: WO2013/111710
PCT Pub. Date: Aug. 1, 2013

(65) Prior Publication Data
US 2014/0079178 A1    Mar. 20, 2014

(30) Foreign Application Priority Data

Jan. 27, 2012  (JP) .................. 2012-015067

(51) Int. Cl.
*A61B 6/03* (2006.01)
*A61B 6/00* (2006.01)
*G06T 11/00* (2006.01)

(52) U.S. Cl.
CPC ................ *A61B 6/52* (2013.01); *A61B 6/032* (2013.01); *A61B 6/463* (2013.01); *A61B 6/465* (2013.01); *A61B 6/5235* (2013.01); *G06T 11/008* (2013.01)

(58) Field of Classification Search
CPC ........... A61B 6/027; A61B 6/032; A61B 6/52; A61B 6/463; A61B 6/465; A61B 6/5235; G01N 23/046; G06T 11/006; G06T 11/008
See application file for complete search history.

(56) References Cited

U.S. PATENT DOCUMENTS 5,513,237 A    4/1996  Nobuta et al.
6,198,791 B1 *  3/2001  He et al. .................. 378/19
(Continued)

FOREIGN PATENT DOCUMENTS

CN    1813635 A    8/2006
JP    3090400       9/2000
(Continued)

OTHER PUBLICATIONS

International Search Report Issued Apr. 2, 2013 in PCT/JP13/051108 Filed Jan. 21, 2013.

(Continued)

*Primary Examiner* — Glen Kao
(74) *Attorney, Agent, or Firm* — Oblon, McClelland, Maier & Neustadt, L.L.P.

(57) ABSTRACT

An X-ray CT apparatus, which is capable of quickly acquiring information for determining whether further CT imaging is required, is provided. The X-ray CT apparatus according to the embodiment comprises a reconstruction processor, a setting unit, and a controller. The reconstruction processor carries out first reconstruction processing to be carried out at a first image thickness based on detection data to be sequentially acquired by X-ray scanning of the desired site of a subject, and second reconstruction processing to be carried out at a second image thickness based on all detection data acquired by the X-ray scanning. The setting unit sets the first image thickness based on the second image thickness set in advance. The controller allows the reconstruction processor to initiate the first reconstruction processing in parallel with the X-ray scanning at the set first image thickness and (Continued)

initiate the second reconstruction processing at the second image thickness once the first reconstruction processing is completed.

9 Claims, 5 Drawing Sheets

(56) References Cited

U.S. PATENT DOCUMENTS

| | | | |
|---|---|---|---|
| 2004/0172292 A1* | 9/2004 | Takekoshi et al. | 705/2 |
| 2007/0036265 A1 | 2/2007 | Jing et al. | |
| 2008/0049889 A1* | 2/2008 | Tsukagoshi et al. | 378/4 |

FOREIGN PATENT DOCUMENTS

| | | |
|---|---|---|
| JP | 2004 267601 | 9/2004 |
| JP | 2006-87544 | 4/2006 |
| JP | 2007 50264 | 3/2007 |
| JP | 2010 131044 | 6/2010 |
| JP | 2012 5894 | 1/2012 |

OTHER PUBLICATIONS

Combined Office Action and Search Report issued Feb. 4, 2015 in Chinese Patent Application No. 201380001185.1 (with English Translation of Category of Cited Documents).

Japanese Office Action dated Oct. 4, 2016 issued for Japanese Patent Application No. 2012-287387, 3 pages, no translation.

* cited by examiner

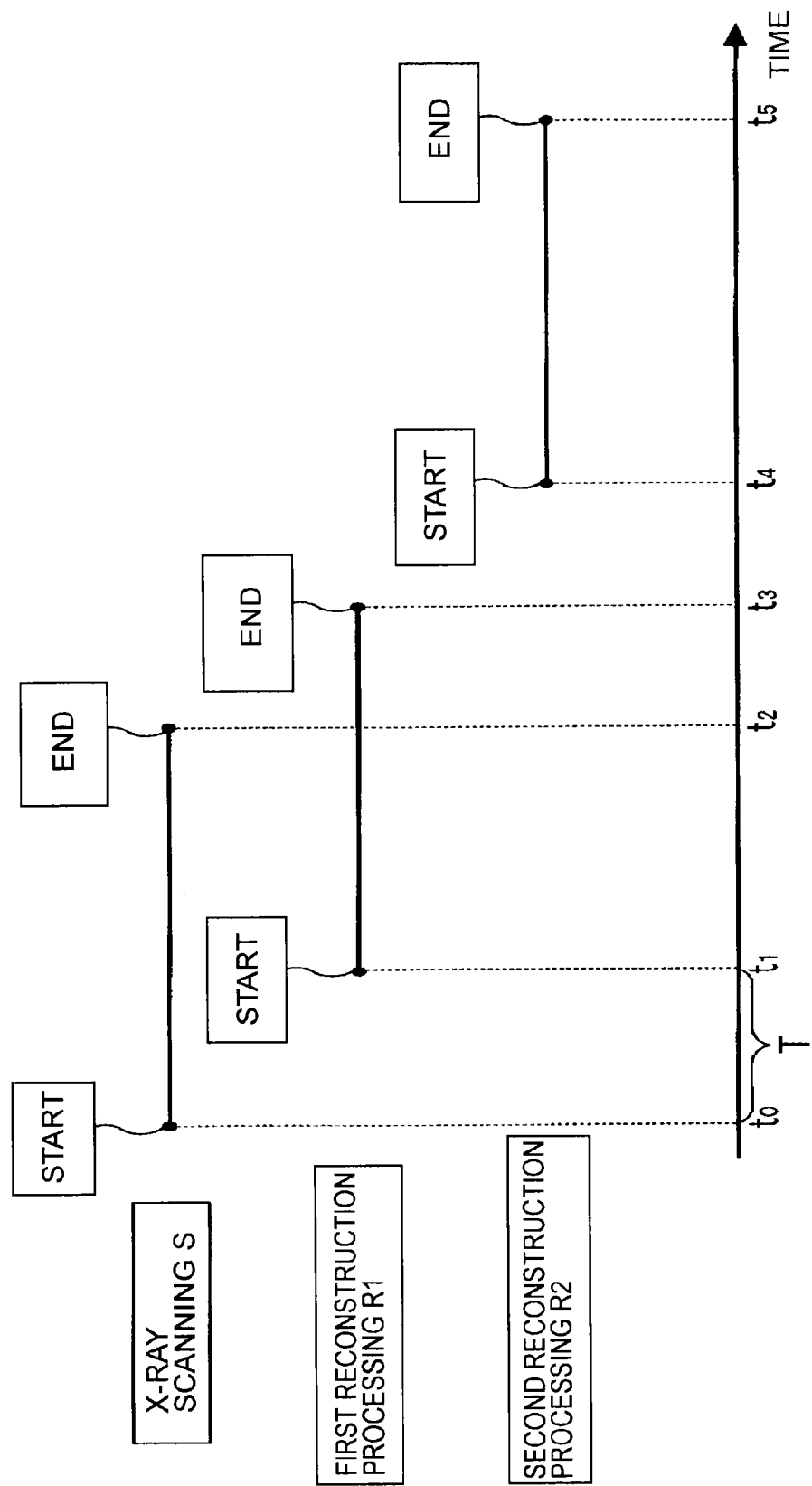

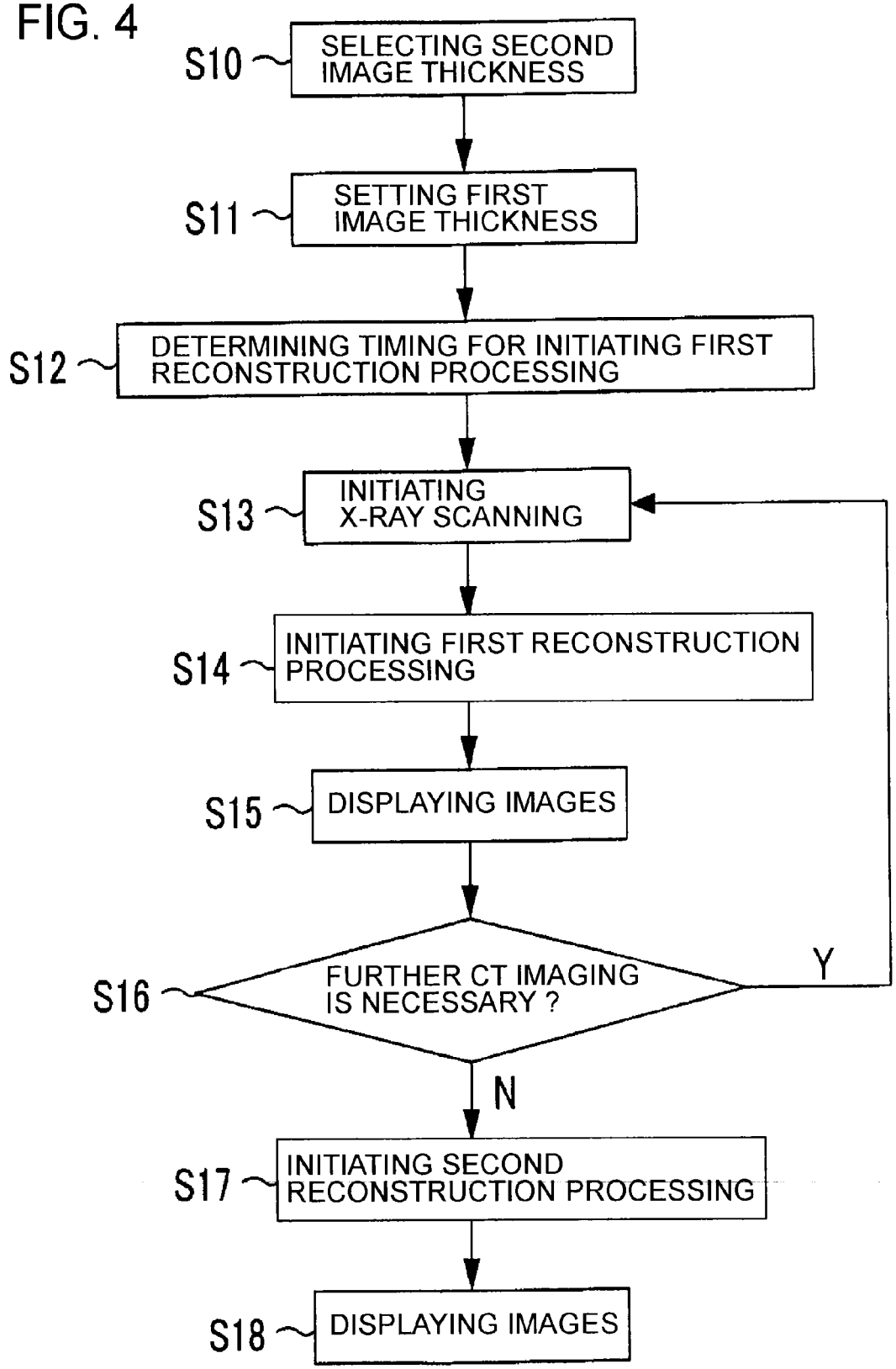

X-RAY CT APPARATUS

TECHNICAL FIELD

The embodiment of the present invention relates to an X-ray CT apparatus.

BACKGROUND ART

An X-ray CT (Computed Tomography) apparatus is an apparatus configured to image the inside of a subject by scanning the subject using X-rays and computer processing the acquired data.

Specifically, an X-ray CT apparatus acquires a plurality of detection data by radiating X-rays onto the subject multiple times from different directions (X-ray scanning) and detecting the X-rays transmitted through the subject using an X-ray detector. The acquired detection data is transmitted to a console device after being A/D-converted by a data acquisition system. The console device creates projection data by applying preprocessing, and the like to the detection data. Subsequently, the console device carries out reconstruction processing based on the projection data, creating volume data based on tomographic image data or a plurality of tomographic image data. The volume data is a data set representing a three-dimensional distribution of a CT value corresponding to a three-dimensional region of the subject.

When a site to be imaged (for example, a site suspected of having a lesion) is not included in the detection data upon carrying out CT imaging using the X-ray CT apparatus, it is necessary to carry out further CT imaging. This makes it necessary to confirm whether the detection data including the site to be imaged has been acquired.

Therefore, the X-ray CT apparatus transmits all of the acquired detection data to the console device once the X-ray scanning is completed, then reconstructs images. Subsequently, a doctor et al. carries out an operation confirming whether the site to be imaged is included in the detection data based on the reconstructed images.

PRIOR ART DOCUMENT

Patent Document

[Patent Document 1] U.S. Pat. No. 3,090,400

SUMMARY OF THE INVENTION

Problems to be Solved by the Invention

There is a case such that a plurality of persons is sequentially examined using a single X-ray CT apparatus (for example, a group medical examination or examination in a large hospital). In this case, it is preferable that the examination time per person be short. Accordingly, there is a demand for quickly determining whether further CT imaging is necessary.

Unfortunately, conventionally, it takes several minutes until reconstruction is completed when reconstruction processing is initiated upon completion of X-ray scanning, making it difficult to conduct an efficient examination. In addition, if further CT imaging is required as a result of confirming the reconstruction-processed images, it becomes problematic in that the previous reconstruction processing is wasted.

The present embodiment intends to solve the above-described problems, with the object thereof to provide an X-ray CT apparatus capable of quickly acquiring information for determining whether further CT imaging is required.

Means for Solving the Problems

The X-ray CT apparatus according to the embodiment comprises a reconstruction processor, a setting unit, and a controller. The reconstruction processor carries out first reconstruction processing to be carried out at a first image thickness based on detection data to be sequentially acquired by X-ray scanning of a desired site of the subject, with second reconstruction processing to be carried out at a second image thickness based on all detection data acquired by the X-ray scanning. The setting unit sets the first image thickness based on the second image thickness set in advance. The controller allows the reconstruction processor to initiate the first reconstruction processing in parallel with the X-ray scanning at the set first image thickness and initiate the second reconstruction processing at the second image thickness once the first reconstruction processing is completed.

BRIEF DESCRIPTION OF THE DRAWINGS

FIG. 2 is a timing chart illustrating operations of the X-ray CT apparatus according to the embodiment.

FIG. 4 is a flowchart illustrating the summary of the operation of the X-ray CT apparatus according to the embodiment.

MODES FOR CARRYING OUT THE INVENTION

The structure of an X-ray CT apparatus 1 according to the embodiment is described with reference to FIG. 1 to FIG. 4. Further, "image" and "image data" may be identified with each other in the present embodiment since they correspond one-to-one with each other.

<Apparatus Structure>

Figure 1:
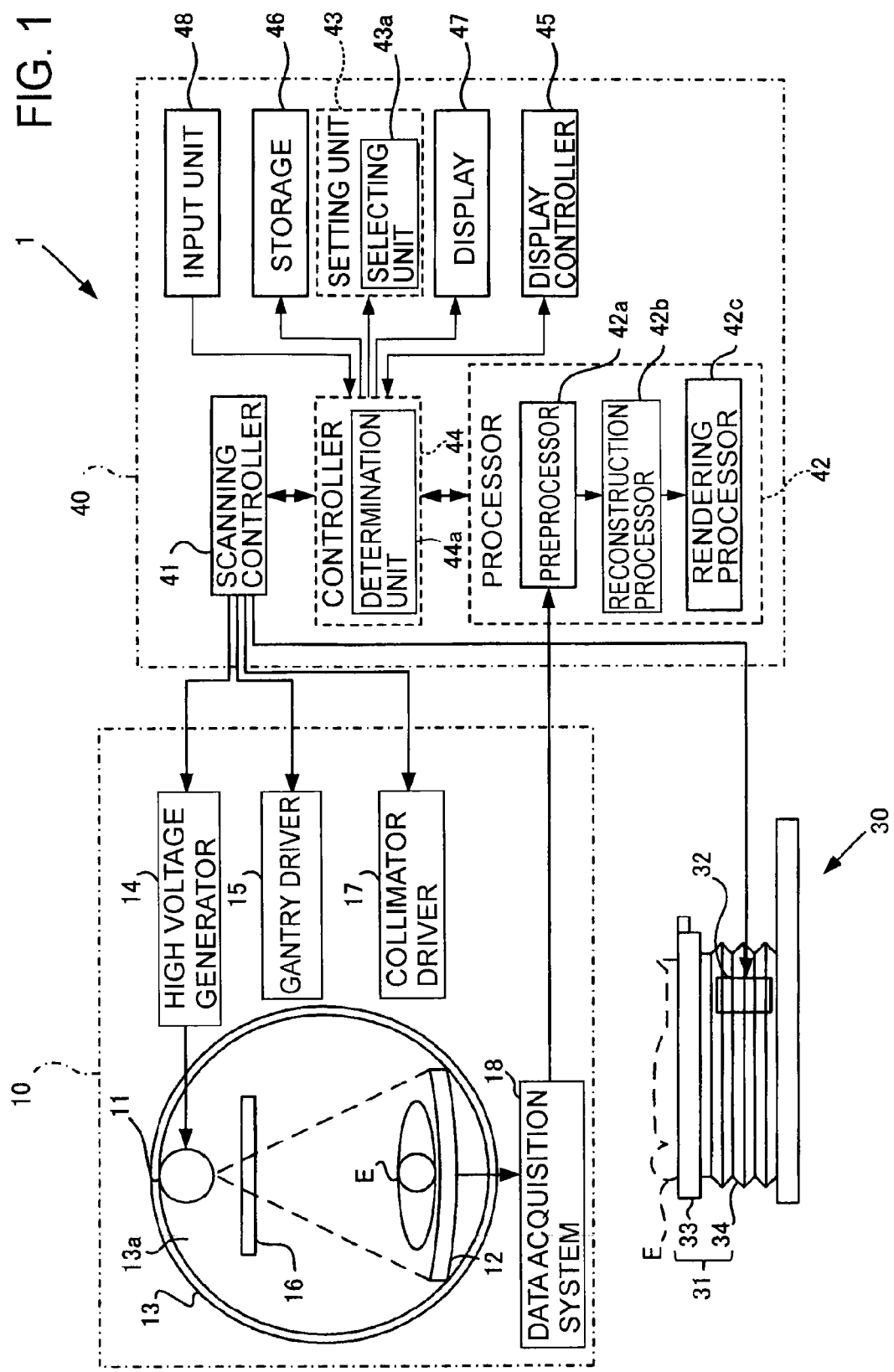
FIG. 1 is a block diagram of an X-ray CT apparatus according to an embodiment.

The X-ray CT apparatus 1 is configured by comprising a gantry apparatus 10, a couch apparatus 30, and a console device 40 as illustrated in FIG. 1.

[Gantry Apparatus]

The gantry apparatus 10 is an apparatus for radiating X-rays onto a subject E, and acquiring detection data of the X-rays transmitted through the subject E. The gantry apparatus 10 comprises an X-ray generator 11, an X-ray detector 12, a rotating body 13, a high voltage generator 14, a gantry driver 15, an X-ray collimator (diaphragm) device 16, a collimator (diaphragm) driver 17, and a data acquisition system 18.

The X-ray generator 11 is configured by comprising an X-ray tube for generating X-rays (for example, a vacuum tube for generating conical or pyramid beams. Not illustrated). The generated X-rays are radiated onto the subject E. The X-ray detector 12 is configured by including a plurality of X-ray detecting elements (not illustrated). The X-ray detector 12 detects X-ray intensity distribution data (hereinafter, sometimes referred to as "detection data") depicting the intensity distribution of the X-rays transmitted through the subject E by the X-ray detecting elements, and outputs this detection data as a current signal. As the X-ray detector 12, for example, a two-dimensional X-ray detector (a face detector) having a plurality of detecting elements respectively arranged in two directions orthogonal to one another (the slice direction and the channel direction) is used. For example, the plurality of X-ray detecting elements includes 320 rows of X-ray detecting elements arranged in the slice direction. Thus, a three-dimensional imaging region with its width in the slice direction can be imaged by a single scanning roll using multiple rows of X-ray detectors (volume scanning). The slice direction corresponds to the rostrocaudal direction of the subject E, while the channel direction corresponds to the rotational direction of the X-ray generator 11.

The rotating body 13 is a member for supporting the X-ray generator 11 and the X-ray detector 12 such that the subject E is sandwiched therebetween. The rotating body 13 has an aperture 13a penetrating in the slice direction. In the gantry apparatus 10, the rotating body 13 is arranged to rotate in a circular orbit around the subject E.

The high voltage generator 14 applies high voltage to the X-ray generator 11. The X-ray generator 11 generates X-rays based on this high voltage. The gantry driver 15 rotatably drives the rotating body 13. The X-ray collimator device 16 provided with a slit (aperture) of a specific width adjusts the fan angle (the spread angle in the channel direction) of the X-rays radiated from the X-ray generator 11 and the cone angle (the spread angle in the slice direction) of the X-rays by changing the width of the slit. The collimator driver 17 drives the X-ray collimator device 16 so that the X-rays generated by the X-ray generator 11 take a specific shape.

The data acquisition system 18 (DAS: Data Acquisition System) acquires the detection data from the X-ray detector 12 (each X-ray detecting element). In addition, the data acquisition system 18 converts the acquired detection data (a current signal) into a voltage signal, periodically integrates and amplifies the voltage signal, then converts the amplified voltage signal into a digital signal. Subsequently, the data acquisition system 18 transmits the detection data converted into the digital signal to the console device 40 (a processor 42 (to be described later)). In the case of carrying out CT fluoroscopy, the data acquisition system 18 shortens the acquiring rate of the detection data.

[Couch Apparatus]

The couch apparatus 30 is an apparatus for mounting and transferring the subject E that is the imaging object. The couch apparatus 30 is provided with a couch 31 and a couch driver 32. The couch 31 is provided with a couch top 33 for mounting the subject E thereon and a base 34 for supporting the couch top 33. The couch driver 32 allows the couch top 33 to transfer in the rostrocaudal direction of the subject E and the direction orthogonal to the rostrocaudal direction. In other words, the couch driver 32 allows the couch top 33 with the subject E mounted thereon to be inserted in or removed from the aperture 13a of the rotating body 13. The couch driver 32 allows the base 34 to transfer the couch top 33 in a vertical direction (the direction orthogonal to the rostrocaudal direction of the subject E).

[Console Device]

A console device 40 is used for the input operation with respect to the X-ray CT apparatus 1. In addition, the console device 40 has a function, and the like, for reconstructing CT image data (tomographic image data and volume data) representing the inner shape of the subject E from the detection data acquired by the gantry apparatus 10. The console device 40 is configured by including a scanning controller 41, a processor 42, a setting unit 43, a controller 44, a display controller 45, a storage 46, a display 47, and an input unit 48.

The scanning controller 41 controls various operations for X-ray scanning. For example, the scanning controller 41 controls the high voltage generator 14 to apply high voltage to the X-ray generator 11. The scanning controller 41 controls the gantry driver 15 to rotatably drive the rotating body 13. The scanning controller 41 controls the collimator driver 17 to operate the X-ray collimator device 16. The scanning controller 41 controls the couch driver 32 to transfer the couch 31.

The processor 42 carries out various processes on the detection data transmitted from the gantry apparatus 10 (data acquisition system 18). The processor 42 is configured to comprise a preprocessor 42a, a reconstruction processor 42b, and a rendering processor 42c.

The preprocessor 42a carries out preprocessing such as logarithmic transformation processing, offset correction, sensitivity correction, and beam hardening correction on the detection data detected by the gantry apparatus 10 (X-ray detector 12), then creates projection data.

The reconstruction processor 42b carries out reconstruction processing for creating CT image data (tomographic image data and volume data) based on the projection data (detection data) created by the preprocessor 42a. Any method, for example, a 2D Fourier transformation method, a convolution/back-projection method, or the like, can be adopted for the reconstruction of tomographic image data. Volume data is created by conducting interpolation-processing on a plurality of reconstructed tomographic image data. For example, any method such as a cone beam reconstruction method, a multi-slice reconstruction method, or an enlargement reconstruction method can be adopted for the reconstruction of the volume data. As described above, it is possible to reconstruct a broad range of volume data by volume scanning using multiple rows of X-ray detectors. In addition, in the case of carrying out CT fluoroscopy, the reconstruction time of the reconstruction processor 42b is shortened, as the acquiring rate of the detection data is short. Accordingly, it is possible to create real-time CT image data corresponding to scanning.

Here, the reconstruction processor 42b according to the present embodiment carries out first reconstruction processing as well as second reconstruction processing.

The first reconstruction processing is carried out in parallel with X-ray scanning at the first image thickness based on the detection data (projection data) sequentially acquired from the X-ray scanning for a desired site of the subject E. The first reconstruction processing is initiated after the initiation of X-ray scanning (initiation timing of the first reconstruction processing is to be described later) and a subsequent certain period, then it is completed within several seconds upon completion of X-ray scanning. The first reconstruction processing has fewer noise rejection filters, and the like, used for the reconstruction processing (processing conditions) than the second reconstruction processing. In other words, the processing conditions of the first reconstruction processing are more simplified than the processing conditions of the second reconstruction processing. Accordingly, for the case in which the reconstruction processor 42b carries out the first reconstruction processing, the time required for the processing is shorter compared to that of the second reconstruction processing. A "desired site" is a site, which is a target of CT imaging (for example, the head, lungs, or the like). The desired site is determined, for example, based on input via the input unit 48.

The second reconstruction processing is carried out at the second image thickness based on all detection data acquired from the X-ray scanning for the desired site upon completion of the first reconstruction processing. In other words, the second reconstruction processing is carried out once the X-ray scanning is completed. The second reconstruction processing has a higher number of noise removing filters, and the like, used for the reconstruction processing (processing conditions) compared to the first reconstruction processing. Accordingly, for the case in which the reconstruction processor 42b carries out the second reconstruction processing, the time required for the processing is longer than the first reconstruction processing. On the other hand, the second reconstruction processing is capable of acquiring CT image data achieving a higher spatial resolution compared to the CT image data acquired from the first reconstruction processing. Images based on such CT image data achieving a high spatial resolution can be used for a doctor et al. to make a definitive diagnosis, for example.

The "image thickness" refers to the data volume (the thickness of data when the reconstruction processing is carried out) when a plurality of projection data (detection data) is reconstructed. The image thickness has an appropriate value for each site of the subject E (for example, the head, and chest); however, an arbitrary value can be set by a doctor et al. In addition, when the image thickness is thick, the data volume becomes large, allowing the information volume to be imaged also be large. Therefore, images based on the CT image data acquired by carrying out the reconstruction processing at a thick image thickness (for example, 5 mm) become images with low contrast, which are averaged as a whole. On the other hand, when the image thickness is thin, the data volume is small, allowing the information volume to be imaged also be small. Therefore, images based on the CT image data acquired by carrying out the reconstruction processing on a thin image thickness (for example, 0.5 mm) become images with high contrast on which sharpened lesion sites, and the like are displayed. Further, the thinner the image thickness is, the shorter the time required for reconstruction processing becomes.

The rendering processor 42c carries out the rendering processing on the volume data created by the processor 42b. For example, the rendering processor 42c carries out MPR display by rendering the volume data created by the reconstruction processor 42b in an arbitrary direction (in other words, the rendering processor 42c creates MPR images). The rendering processor 42c can create, as MPR images, axial images, sagittal images, and coronal images, which are three orthogonal sections and oblique images which are arbitrary sectional images.

The setting unit 43 sets the first image thickness based on a predetermined second image thickness. The first image thickness is the value used when the first reconstruction processing is carried out. The second image thickness is the value used when the second reconstruction processing is carried out. The reconstruction processor 42b can create CT image data, which is the origin of the image used for confirming diagnoses, and the like by carrying out the second reconstruction processing based on the second image thickness.

In addition, according to the present embodiment, the setting unit 43 sets an image thickness identical with the second image thickness as the first image thickness. The reconstruction processor 42b carries out the first reconstruction processing on the image thickness identical with the second image thickness. In this case, the first reconstruction processing and the second reconstruction processing have different processing conditions (the number of noise removing filters used for the reconstruction processing, and the like).

In the present embodiment, the setting unit 43 has a selecting unit 43a. The selecting unit 43a selects the second image thickness corresponding to the desired site input by the input unit 48, and the like from a plurality of second image thicknesses stored in the storage 46. The setting unit 43 sets the first image thickness based on the selected second image thickness.

The storage 46 generally stores a plurality of examination plan data corresponding to the site of the subject E (for example, examination plan data for head scanning, examination plan data for lung scanning, etc.). The scanning conditions such as the scanning rate and imaging range are set in the examination plan data. In addition, a specific image thickness is related to the scanning conditions in the examination plan data. Further, the processing conditions when carrying out the reconstruction processing may also be related to the scanning conditions.

Here, after selecting the site applied to the X-ray scanning through the input unit 48 or the like, the selecting unit 43a specifies the examination plan data corresponding to this site from a plurality of examination plan data. Subsequently, the selecting unit 43a selects the image thickness set in the specified examination plan data as the second image thickness. The setting unit 43 sets the first image thickness based on the selected second image thickness. In the present embodiment, the setting unit 43 sets the value identical with the selected second image thickness as the first image thickness. The selected image thickness (the second image thickness) is a value suitable when the desired site is reconstructed. Accordingly, a reliable image can be acquired by carrying out the first reconstruction processing using the same value as the first image thickness.

Setting of the first image thickness by the setting unit 43 is not limited to the above-described methods. For example, it is possible to input through the input unit 48 the image thickness when carrying out the second reconstruction processing each time. In this case, the setting unit 43 sets the same numeric value as the numeric value of the input image thickness as the first image thickness.

In addition, the setting unit 43 also can set the scanning conditions based on the selected second image thickness. As described above, the specific image thickness (the second image thickness) is related to the specific scanning conditions (scanning rate, imaging region, and the like) in the examination plan data. Accordingly, the setting unit 43 can set the scanning rate, imaging region, and the like, when carrying out X-ray scanning based on the scanning conditions related to the second image thickness selected by the selecting unit 43a.

The controller 44 completely controls the X-ray CT apparatus 1 by controlling the operations of the gantry apparatus 10, the couch apparatus 30, and the console device 40.

The controller 44 according to the present embodiment includes a determination unit 44a. The determination unit 44a determines the timing for initiating the first reconstruction processing based on the first image thickness set by the setting unit 43.

Here, the first reconstruction processing cannot be initiated unless at least the detection data (projection data) corresponding to the first image thickness is acquired. The time T from the initiation of X-ray scanning ($t_0$)) until this detection data is first acquired is the sum ($T=T_1+T_2$) of time $T_1$ acquired from the scanning rate of X-ray scanning (the rotational rate of the X-ray generator 11) and the value of the first image thickness and time $T_2$ from transmission of the detection data acquired by this X-ray scanning to the console device 40 until preprocessing is completed.

The determination unit 44a first obtains time T according to a specific example. Subsequently, the determination unit 44a determines the time $t_1$ when the time T has passed from the initiation of X-ray scanning ($t_0$)) as the timing for initiating the first reconstruction processing. The controller 44 initiates the first reconstruction processing at the determined timing. Thus, the controller 44 allows the reconstruction processor 42b to initiate the first reconstruction processing at time $t_1$ when the necessary detection data (data corresponding to the first image thickness) has been acquired, making it possible to quickly acquire desired images (for example, images for determining whether further CT imaging is necessary).

An example of control by means of the controller 44 is described using the timing chart illustrated in FIG. 2. The horizontal axis in FIG. 2 represents time. The top line indicates an X-ray scanning S. The middle line indicates a first reconstruction processing R1. The bottom line indicates a second reconstruction processing R2. As illustrated in FIG. 2, the controller 44 allows the reconstruction processor 42b to initiate the first reconstruction processing R1 at the first image thickness at timing (time $t_1$) determined by the determination unit 44a upon initiation of X-ray scanning S ($t_0$). The first reconstruction processing R1 is completed ($t_3$) within several seconds (for example, 2 to 3 seconds) upon completion of X-ray scanning S ($t_2$) since the processing conditions thereof are more simplified compared to that of the second reconstruction processing R2. For the case in which further X-ray scanning is deemed unnecessary as a result of confirmation of the images by a doctor et al. based on the volume data, and the like acquired from the first reconstruction processing R1, the controller 44 allows the reconstruction processor 42b to initiate the second reconstruction processing R2 ($t_4$) at the second image thickness.

The time $t_3$ when the first reconstruction processing R1 is completed can be adjusted by changing, for example, the conditions such as the number of filters used for the first image thickness and the reconstruction processing based on the instruction input of the input unit 48, or the like. The changed conditions can be stored in the storage 46 as new examination plan data.

The display controller 45 carries out various controls for image display. For example, the display controller 45 allows the display 47 to display images based on the first reconstruction processing (for example, MPR images acquired by rendering the volume data acquired from the first reconstruction processing). As described above, it is possible to acquire images according to the first reconstruction processing within several seconds upon completion of scanning. Accordingly, a doctor et al. can quickly determine whether further CT imaging is necessary by displaying the images acquired from the first reconstruction processing. In addition, it is also possible to stop the second reconstruction processing of the reconstruction processor 42b since the second reconstruction processing is initiated upon completion of the first reconstruction processing. In other words, for cases in which a doctor et al. determine that further scanning is necessary as a result of confirmation of the images based on the first reconstruction processing, the doctor et al. input instructions into the X-ray CT apparatus 1 so as to prevent the X-ray CT apparatus 1 from carrying out the second reconstruction processing, through the input unit 48, or the like. Based on this input of instructions, the controller 44 controls the reconstruction processor 42b not to initiate the second reconstruction processing. Therefore, it is not necessary for the X-ray CT apparatus 1 (the reconstruction processor 42b) to carry out wasteful reconstruction processing.

In the case of displaying a plurality of images based on the first reconstruction processing (for example, tomographic images), the display controller 45 allows a desired target (lesion site, and the like) in these images to be displayed at a rate allowing the images to be identified. In other words, the display controller 45 allows images to be displayed at a rate such that a doctor et al. may easily confirm these images.

In addition, the display controller 45 can allow the display 47 to display desired images from the plurality of images based on the first reconstruction processing according to the instruction input from outside.

Figure 3A:
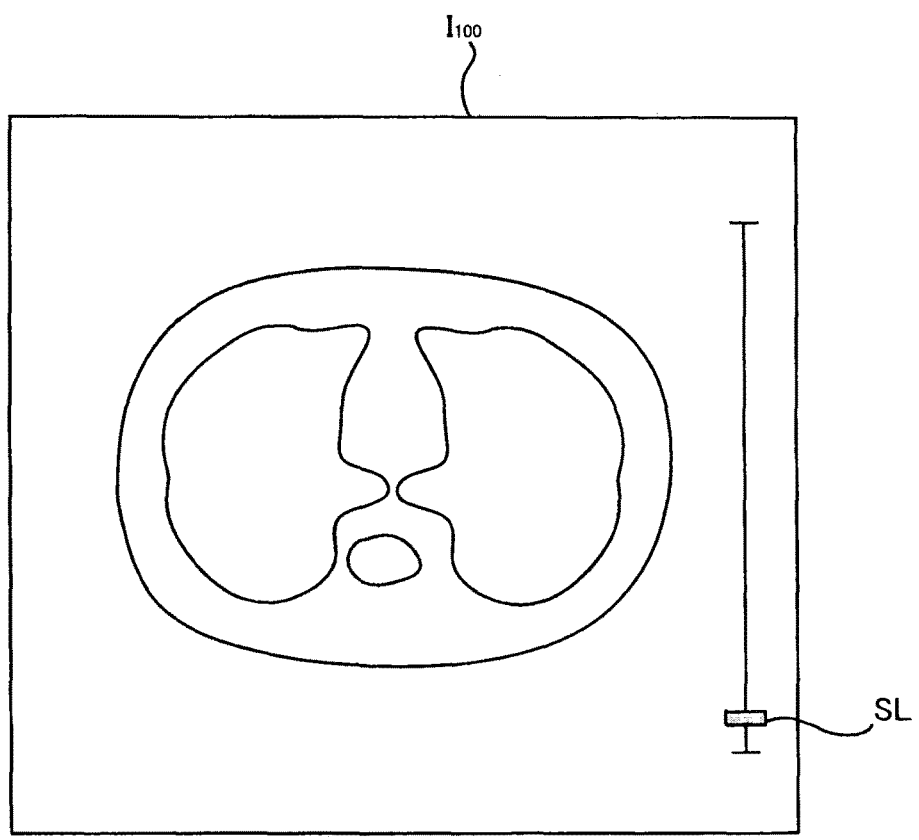
FIG. 3A is a drawing illustrating a display screen of the X-ray CT apparatus according to the embodiment.
Figure 3B:
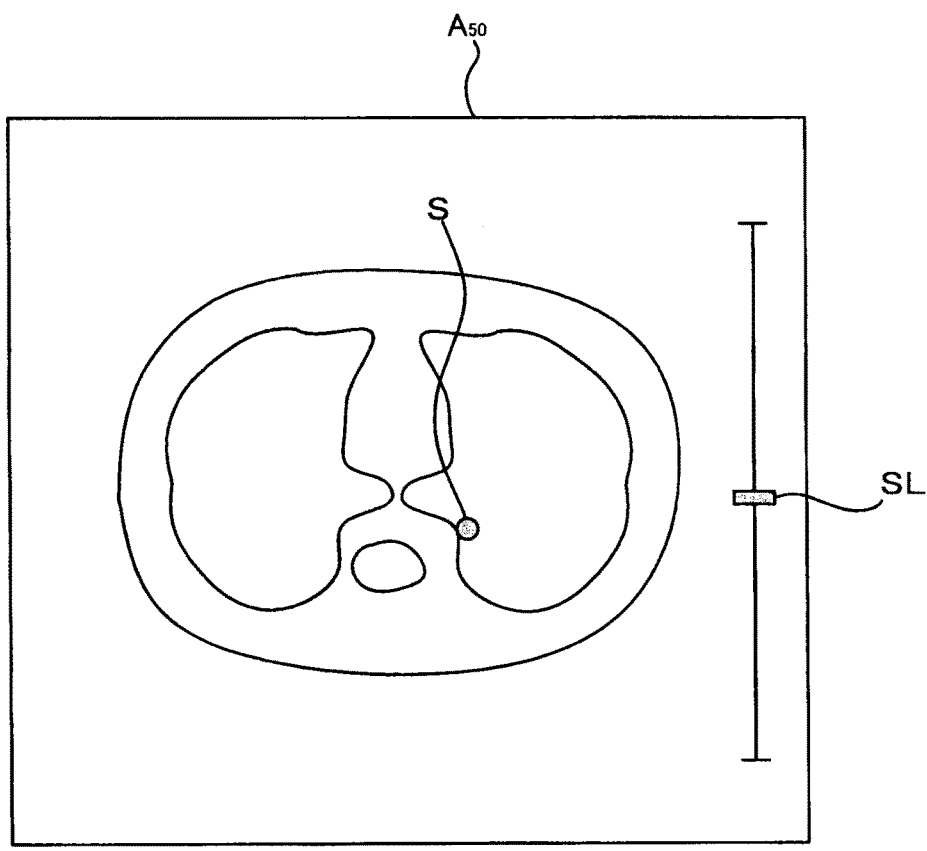
FIG. 3B is a drawing illustrating a display screen of the X-ray CT apparatus according to the embodiment.

For example, when a plurality of tomographic images $I_1$ to $I_{1\,0\,0}$ is obtained based on the first reconstruction processing, the display controller 45 allows the display 47 to sequentially display each image. FIG. 3A and FIG. 3B illustrate an example of the display screen of the display 47. Images (the tomographic image $I_{1\,0\,0}$ or the tomographic image $I_{5\,0}$) and a slide bar SL are displayed on the display screen of the display 47 in FIG. 3A and FIG. 3B.

A doctor et al. can arbitrarily switch the images displayed on the display 46 via the input unit 48 (so-called browse function). The images are switched, for example, by vertically sliding the slide bar SL via the operation of the input unit 48 by a doctor et al. The operation of image switching is an example of "instruction input from outside."

If the slide bar SL is operated with the tomographic image $I_{1\,0\,0}$ displayed on the display 47 (refer to FIG. 3A) according to a specific example, the display controller 45 allows the display 47 to display an image $I_k$ (k=1 to 100) corresponding to the transfer of the slide bar SL. In other words, the display controller 45 allows the display 47 to display a tomographic image $I_{5\,0}$ with a desired target S illustrated in FIG. 3B displayed. The doctor et al. can confirm that the desired target is included in the detection data acquired from X-ray scanning once having confirmed the tomographic image $I_{5\,0}$. Accordingly, the doctor et al. can easily determine that further CT imaging (scanning) is unnecessary.

The storage 46 is configured by a semiconductor storage such as RAM and ROM. The storage 46 stores the detection data and the projection data, or the reconstructed CT image data, and the like.

The display 47 is configured by an arbitrary display device such as an LCD (Liquid Crystal Display) or a CRT (Cathode Ray Tube) display.

The input unit 48 is used as an input device for carrying out various operations on the console device 40. The input unit 48 is configured by, for example, a keyboard, a mouse, a track ball, a joystick, and the like. In addition, a touch panel displayed on the display 47 can be also used as the input unit 48.

<Operations>

Next, an example of operations of the X-ray CT apparatus 1 according to the present embodiment is described with reference to FIG. 4. Here, the case in which X-ray scanning is carried out for a certain site of the subject E is described.

The selecting unit 43a reads the examination plan data corresponding to the site on which the X-ray scanning is carried out from the storage 46. Subsequently, the selecting unit 43a selects the image thickness set in this examination plan data as the second image thickness (S10).

The setting unit 43 sets the image thickness identical with the second image thickness selected in S10 as the first image thickness (S11).

The determination unit 44a determines the timing for initiating the first reconstruction processing based on the first image thickness set in S11 (S12). Specifically, the determination unit 44a determines time T based on time T1 according to the scanning rate and the first image thickness set in S11 and time T2 until the preprocessing of the detection data acquired from this scanning is completed. Subsequently, the determination unit 44a determines the time $t_1$ when time T has passed from the initiation of X-ray scanning as the timing for initiating the first reconstruction processing.

The X-ray CT apparatus 1 initiates the X-ray scanning once the above-described settings are completed (S13).

At the timing determined in S12 once the X-ray scanning is initiated, the reconstruction processor 42b initiates the first reconstruction processing at the first image thickness set in S11 (S14). The first image thickness is, as set in S11, the image thickness identical with the second image thickness.

The display controller 45 displays images based on the first reconstruction processing on the display 47 once this processing is completed (S15). The first reconstruction processing has processing conditions more simplified than the second reconstruction processing. Accordingly, the display controller 45 allows the display 47 to display the images based on the first reconstruction processing within several seconds upon completion of scanning.

Once a doctor et al. confirm the displayed images to determine that further CT imaging is necessary (Y in S16), the operations of S13 to S15 are carried out again.

On the other hand, when further CT imaging is unnecessary (N in S16), the reconstruction processor 42b initiates the second reconstruction processing at the second image thickness selected in S10 (S17). The display controller 45 displays images based on the second reconstruction processing on the display 47 upon completion of the processing (S18).

The second reconstruction processing has a higher number of filters, and the like used compared to the first reconstruction processing. Accordingly, the image to be displayed in S18 achieves a higher spatial resolution compared to the image to be displayed in S15. In other words, the image to be displayed in S18 is sufficient for a doctor et al. to make a definitive diagnosis.

Further, the scanning controller 41, the processor 42, the controller 44, and the display controller 45 may be configured by, for example, a processing apparatus (not illustrated) such as CPU (Central Processing Unit), GPU (Graphic Processing Unit), or ASIC (Application Specific Integrated Circuit) and a storing device (not illustrated) such as ROM (Read Only Memory), RAM (Random Access Memory), or HDD (Hard Disc Drive). Scanning control programs for executing functions of the scanning controller 41 are stored in the storing device. In addition, processing programs for executing functions of the processor 42 are stored in the storing device. Control programs for executing functions of the controller 44 are stored in the storing device. Display control programs for executing functions of the display controller 45 are also stored in the storing device. The processing apparatus such as CPU executes the functions of each unit by executing respective programs stored in the storing device.

<Operations and Effects>

The operations and effects of the present embodiment are described.

The X-ray CT apparatus 1 of the present embodiment comprises the reconstruction processor 42b, the setting unit 43, and the controller 44. The reconstruction processor 42b carries out the first reconstruction processing to be carried out at the first image thickness based on detection data to be sequentially acquired by X-ray scanning the desired site of the subject E, and the second reconstruction processing to be carried out at the second image thickness based on all detection data acquired by the X-ray scanning. The setting unit 43 sets the first image thickness based on the second image thickness set in advance. The controller 44 allows the reconstruction processor 42b to initiate the first reconstruction processing in parallel with the X-ray scanning on the set first image thickness and initiate the second reconstruction processing at the second image thickness once the first reconstruction processing is completed.

Specifically, the setting unit 43 sets the image thickness identical with the second image thickness as the first image thickness. The controller 44 initiates the first reconstruction processing and the second reconstruction processing under different processing conditions.

Thus, the setting unit 43 sets the first image thickness based on the second image thickness set in advance. The second image thickness is an image thickness used for reconstructing the image used for definitive diagnosis, and the like. Accordingly, images based on the CT image data acquired by the first reconstruction processing become reliable images by making the first image thickness in the first reconstruction processing into a value identical with the second image thickness. Subsequently, the controller 44 allows the reconstruction processor 42b to initiate the first reconstruction processing (the processing conditions simpler than that of the second reconstruction processing) in parallel with the X-ray scanning at the first image thickness. It is possible to quickly acquire the images based on the CT image data by carrying out the first reconstruction processing in parallel with the X-ray scanning as described above. In other words, the X-ray CT apparatus 1 of the present embodiment makes it possible to quickly acquire information for determining whether further CT imaging is necessary.

In addition, the X-ray CT apparatus 1 of the present embodiment comprises the input unit 48 and the storage 46. The storage 46 stores the second image thickness corresponding to each site of the subject E. The setting unit 43 comprises the selecting unit 43a. The selecting unit 43a selects the second image thickness corresponding to the desired site input by the input unit 48 from a plurality of second image thicknesses stored in the storage 46. Then, the setting unit 43 sets the first image thickness based on the selected second image thickness.

The first reconstruction processing can be carried out at an image thickness suitable for reconstructing the detection data in the desired site for carrying out X-ray scanning by selecting the second image thickness corresponding to the site for carrying out X-ray scanning from the plurality of second image thicknesses stored in advance as described above. Accordingly, according to the X-ray CT apparatus 1 of the present embodiment, it is possible to quickly acquire the information for determining whether further CT imaging is required.

In addition, the storage 46 in the X-ray CT apparatus 1 of the present embodiment stores the second image thickness and the specific scanning conditions in relation to each other.

The setting unit 43 sets the scanning conditions based on the selected second image thickness.

The X-ray scanning can be carried out under the conditions suitable for the set image thickness by carrying out X-ray scanning based on the scanning conditions related to the image thickness (the second image thickness) set in advance as described above. Therefore, according to the X-ray CT apparatus 1 of the present embodiment, it is possible to reliably acquire the information for determining whether further CT imaging is required.

Further, the controller 44 in the X-ray CT apparatus 1 of the present embodiment comprises the determination unit 44a. The determination unit 44a determines the initiation timing of the first reconstruction processing based on the time obtained from the set first image thickness and the scanning rate of the X-ray scanning. The controller 44 initiates the first reconstruction processing at the determined initiation timing.

As described above, it is possible to initiate reconstruction processing when the minimum and necessary detection data for the first reconstruction processing is prepared by determining the initiation timing of the first reconstruction processing based on the time obtained from the set first image thickness. Accordingly, the first reconstruction processing can be quickly carried out. In other words, it is possible to quickly acquire the information for determining whether further CT imaging is required.

In addition, the X-ray CT apparatus 1 of the present embodiment comprises the display 47 and the display controller 45. The display controller 45 allows the display 47 to display the images obtained from the first reconstruction processing.

A doctor et al. refer to the images obtained by the first reconstruction processing by displaying these images as described above, making it possible to quickly determine whether further CT imaging is required.

Further, the display controller 45 in the X-ray CT apparatus 1 of the present embodiment allows the images obtained from the first reconstruction processing to be displayed at a rate such that the desired subjects in these images can be identified.

As described above, the display controller 45 allows the images to be displayed at the rate such that the desired subjects in the images can be identified, so as to provide images which can be easily observed by a doctor et al. As a result, it is possible to quickly determine whether further CT imaging is required.

Furthermore, the display controller 45 in the X-ray CT apparatus 1 of the present embodiment allows the display 47 to display desired images from a plurality of images obtained from the first reconstruction processing based on instructions input from outside.

It is possible for a doctor et al. to easily confirm images (images with a lesion site, or the like displayed) for determining whether further CT imaging is required by displaying desired images from a plurality of images as described above.

(Modified Example)

It is not always necessary for the image thickness for carrying out reconstruction processing to be the same value between the second reconstruction processing and the first reconstruction processing. For example, the images based on the first reconstruction processing are satisfied if it is possible to determine whether further CT imaging is required from these images. Accordingly, the images based on the first reconstruction processing may be a lower spatial resolution compared to the images based on the second reconstruction processing.

As a specific example, the image thickness different from the second image thickness is set in advance along with the value of the second image thickness in the examination plan data. Subsequently, when the site on which X-ray scanning is carried out is selected from the input unit 48 or the like, the selecting unit 43a identifies the examination plan data corresponding to this site from a plurality of examination plan data. The selecting unit 43a then selects the second image thickness related to the identified data. Further, the setting unit 43 sets the image thickness corresponding to the selected second image thickness as the first image thickness.

It is possible to more quickly acquire the information for determining whether further CT imaging is required by changing the first image thickness of the first reconstruction processing and the second image thickness of the second reconstruction processing as described above. For example, it is possible to shorten the time required for the first reconstruction processing by making the first image thickness thinner than the second image thickness. Accordingly, the display controller 45 can more quickly display the images based on the first reconstruction processing.

Some embodiments of the present invention have been described above; however, these embodiments are merely presented as examples without intending to limit the scope of the invention. These embodiments can be implemented in various other modes, and various omissions, replacements, and changes can be made without departing form the scope of the invention. These embodiments and their modifications are included not only within the scope and spirit of the invention but also in the invention set forth in the claims and any scope equivalent thereto.

DESCRIPTION OF SYMBOLS

1 X-ray CT apparatus
10 gantry apparatus
11 X-ray generator
12 X-ray detector
13 rotating body
14 high voltage generator
15 gantry driver
16 X-ray collimator device
17 collimator driver
18 data acquisition system
30 couch apparatus
32 couch driver
33 couch top
34 base
40 console device
41 scanning controller
42 processor
42a preprocessor
42b reconstruction processor
42c rendering processor
43 setting unit
43a selecting unit
44 controller
44a specifying unit
45 display controller
46 storage
47 display
48 input unit

The invention claimed is:

1. An X-ray CT apparatus, comprising:
   a reconstruction processor configured to carry out first reconstruction processing to be carried out at a first image thickness based on detection data to be sequentially acquired by X-ray scanning the desired site of a subject, and to carry out second reconstruction processing to be carried out at a second image thickness based on all detection data acquired by the X-ray scanning;
   a setting unit configured to set the first image thickness based on the second image thickness set in advance so that the first image thickness is less than the second image thickness; and
   a controller configured to allow the reconstruction processor to initiate the first reconstruction processing in parallel with the X-ray scanning at the set first image thickness, to judge whether further X-ray scanning is necessary or not once the first reconstruction processing is completed, to allow the reconstruction processor to initiate the second reconstruction processing at the second image thickness when further X-ray scanning is judged unnecessary, and to not allow the reconstruction processor to initiate the second reconstruction processing when further X-ray scanning is judged necessary.

2. The X-ray CT apparatus according to claim 1, wherein:
   the controller is configured to initiate the first reconstruction processing and the second reconstruction processing under different processing conditions.

3. The X-ray CT apparatus according to claim 1, comprising:
   an input unit; and
   a storage configured to store the second image thicknesses corresponding to each site of the subject,
   wherein the setting unit comprises a selecting unit configured to select the second image thickness corresponding to the desired site input by the input unit from a plurality of second image thicknesses stored in the storage, and the setting unit is configured to set the first image thickness based on the selected second image thickness.

4. The X-ray CT apparatus according to claim 3, wherein:
   the storage is configured to store the second image thicknesses and specific scanning conditions in relation to each other; and
   the setting unit is configured to set the scanning conditions based on the selected second image thickness.

5. The X-ray CT apparatus according to claim 1,
   wherein the controller comprises a determining unit configured to determine initiation timing of the first reconstruction processing based on the time obtained from the set first image thickness and a scanning rate of the X-ray scanning, so that the controller initiates the first reconstruction processing at the determined initiation timing.

6. The X-ray CT apparatus according to claim 5, wherein the determining unit determines initiation timing of the first reconstruction processing based on the time obtained from the set first image thickness and a scanning rate of the X-ray scanning, so that the controller initiates the first reconstruction processing when minimum and necessary detection data for the first reconstruction processing is prepared.

7. The X-ray CT apparatus according to claim 1, comprising:
   a display; and
   a display controller configured to allow the display to display images obtained from the first reconstruction processing.

8. The X-ray CT apparatus according to claim 7, wherein the display controller is configured to allow the images obtained from the first reconstruction processing to be displayed at a rate such that the desired subjects in these images can be identified.

9. The X-ray CT apparatus according to claim 7, wherein the display controller is configured to allow the display to display desired images from the plurality of images obtained from the first reconstruction processing based on instructions input from outside.

* * * * *